United States Patent
Hsu et al.

(10) Patent No.: US 12,415,065 B2
(45) Date of Patent: Sep. 16, 2025

(54) ARTIFICIAL RETINAL PROSTHESIS FOR PROVIDING COLOR VISUAL PERCEPTION

(71) Applicant: IRIDIUM MEDICAL TECHNOLOGY CO., LTD., Hsinchu (TW)

(72) Inventors: Feng-Hsiung Hsu, Hsinchu (TW); Yung-Chan Chen, Hsinchu (TW); Long-Sheng Fan, Hsinchu (TW); Lee Lin, Hsinchu (TW)

(73) Assignee: IRIDIUM MEDICAL TECHNOLOGY CO., LTD., Hsin-Chu (TW)

(*) Notice: Subject to any disclaimer, the term of this patent is extended or adjusted under 35 U.S.C. 154(b) by 548 days.

(21) Appl. No.: 17/704,815

(22) Filed: Mar. 25, 2022

(65) Prior Publication Data
US 2022/0211999 A1 Jul. 7, 2022

Related U.S. Application Data

(63) Continuation-in-part of application No. 16/230,218, filed on Dec. 21, 2018, now abandoned.

(60) Provisional application No. 62/610,004, filed on Dec. 22, 2017.

(51) Int. Cl.
*A61N 1/05* (2006.01)

(52) U.S. Cl.
CPC .................. *A61N 1/0543* (2013.01)

(58) Field of Classification Search
None
See application file for complete search history.

(56) References Cited

U.S. PATENT DOCUMENTS

| | | | |
|---|---|---|---|
| 6,804,560 B2 | 10/2004 | Nisch et al. | |
| 7,751,896 B2 | 7/2010 | Graf et al. | |
| 9,155,881 B2 | 10/2015 | Fan | |
| 2008/0294224 A1* | 11/2008 | Greenberg | A61N 1/0543 607/54 |
| 2010/0211168 A1 | 8/2010 | Goertz et al. | |
| 2011/0202132 A1 | 8/2011 | Meijer | |
| 2014/0121738 A1* | 5/2014 | Arafune | A61N 1/0543 607/116 |
| 2015/0049231 A1 | 2/2015 | Chen et al. | |
| 2016/0038739 A1 | 2/2016 | Liu et al. | |

(Continued)

*Primary Examiner* — Erica S Lee
(74) *Attorney, Agent, or Firm* — MUNCY, GEISSLER, OLDS & LOWE, P.C.

(57) ABSTRACT

An artificial retinal prosthesis is disclosed, which comprises a plurality of pixel group units to output a spatiotemporal electrical stimulation for inducing color perception. Each of the pixel group units comprises a main pixel unit and at least one surrounding pixel unit. The main pixel unit and the surrounding pixel unit respectively outputs an electrical stimulation waveform according to a first stimulation cycle and a second stimulation cycle. Both of the first stimulation cycle and the second stimulation cycle have a first-half duration and a second-half duration. The first-half duration of the first stimulation cycle has inactive period greater than 20% and less than 80% and the rest of the first stimulation cycle is active period. The second-half duration of the first stimulation cycle is inactive period. The first-half duration of the second stimulation cycle is active period and the second-half duration of the second stimulation cycle is inactive period.

4 Claims, 9 Drawing Sheets

(56) References Cited

U.S. PATENT DOCUMENTS

2016/0118429 A1    4/2016  Otsuji
2016/0256677 A1    9/2016  Song et al.
2017/0224998 A1*   8/2017  Gefen ..................... A61F 9/00

* cited by examiner

| Frame | 1 | 2 | 3 | 4 | 5 | 6 | 7 |
|---|---|---|---|---|---|---|---|
| On/Off | _ | _ | _ | _ | | | | | _ |

| | Column 1 | Column 2 | Column 3 | Column 4 | Column 5 | Column 6 |
|---|---|---|---|---|---|---|
| Row 1 | D: ___ \|\|\|\| | D: ___ \|\|\|\| | D: ___ \|\|\|\| | D: ___ \|\|\|\| | D: ___ \|\|\|\| | D: ___ \|\|\|\| |
| Row 2 | R: _____ \|\| | D: ___ \|\|\|\| | G: ____ \|\|_ | D: ___ \|\|\|\| | B: ___ \|\|__ | D: ___ \|\|\|\| |
| Row 3 | D: ___ \|\|\|\| | D: ___ \|\|\|\| | D: ___ \|\|\|\| | D: ___ \|\|\|\| | D: ___ \|\|\|\| | D: ___ \|\|\|\| |
| Row 4 | B: ___ \|\|__ | D: ___ \|\|\|\| | R: _____ \|\| | D: ___ \|\|\|\| | G: ____ \|\|_ | D: ___ \|\|\|\| |
| Row 5 | D: ___ \|\|\|\| | D: ___ \|\|\|\| | D: ___ \|\|\|\| | D: ___ \|\|\|\| | D: ___ \|\|\|\| | D: ___ \|\|\|\| |
| Row 6 | G: ____ \|\|_ | D: ___ \|\|\|\| | B: ___ \|\|__ | D: ___ \|\|\|\| | R: _____ \|\| | D: ___ \|\|\|\| |
| Row 7 | D: ___ \|\|\|\| | D: ___ \|\|\|\| | D: ___ \|\|\|\| | D: ___ \|\|\|\| | D: ___ \|\|\|\| | D: ___ \|\|\|\| |

Fig. 5

| Frame | 1 | 2 | 3 | 4 | 5 | 6 | 7 |
|---|---|---|---|---|---|---|---|
| On/Off | _ | _ | _ | _ | _ | | | | |

|  | Column 1 | Column 2 | Column 3 | Column 4 | Column 5 | Column 6 |
|---|---|---|---|---|---|---|
| Row 1 | D: ___\|\|\| | D: ___\|\|\| | D: ___\|\|\| | D: ___\|\|\| | D: ___\|\|\| | D: ___\|\|\| |
| Row 2 | R: _____\|\| | D: ___\|\|\| | G: ____\|\|_ | D: ___\|\|\| | B: ___\|\|__ | D: ___\|\|\| |
| Row 3 | D: ___\|\|\| | D: ___\|\|\| | D: ___\|\|\| | D: ___\|\|\| | D: ___\|\|\| | D: ___\|\|\| |
| Row 4 | B: ___\|\|__ | D: ___\|\|\| | R: _____\|\| | D: ___\|\|\| | G: ____\|\|_ | D: ___\|\|\| |
| Row 5 | D: ___\|\|\| | D: ___\|\|\| | D: ___\|\|\| | D: ___\|\|\| | D: ___\|\|\| | D: ___\|\|\| |
| Row 6 | G: ____\|\|_ | D: ___\|\|\| | B: ___\|\|__ | D: ___\|\|\| | R: _____\|\| | D: ___\|\|\| |
| Row 7 | D: ___\|\|\| | D: ___\|\|\| | D: ___\|\|\| | D: ___\|\|\| | D: ___\|\|\| | D: ___\|\|\| |

Fig. 6

ARTIFICIAL RETINAL PROSTHESIS FOR PROVIDING COLOR VISUAL PERCEPTION

CROSS-REFERENCE TO RELATED APPLICATION

The present application is a continuation-in-part application of U.S. patent application Ser. No. 16/230,218, filed on Dec. 21, 2018, which claims the benefit of U.S. Provisional Patent Application No. 62/610,004, entitled "System for Artificial Retina Prosthesis," which was filed on Dec. 22, 2017, and the disclosure of which is incorporated herein by reference in its entirety.

FIELD OF THE INVENTION

The present invention relates to an artificial retinal prosthesis, and more particularly to an artificial retinal prosthesis for providing color visual perception.

BACKGROUND OF THE INVENTION

Currently, among the patients with visual deterioration, some patients choose to implant an artificial retina to improve their vision. At present, expensive artificial retinas of the commercial standard with low pixels have a limited improvement on the quality of life of patients. In view of this, many companies as well as academic and research institutes have begun to actively invest in the improvement of microsystem for artificial retina.

In order to give the users a more comfortable visual experience, many R&D teams are actively making improvements on the image resolution. For example, U.S. Pat. No. 7,751,896 B2, No. U.S. Pat. No. 6,804,560 B2 improve the signal transmission in the artificial retina by adding components such as an amplifier or a photosensitive reference component to the circuit, so that the electrical stimulation signals of the artificial retina are more even, when the patient wears the above artificial retina, it is just like the response of eyes to ambient light conditions under natural conditions. There are also other teams that focus on the colors of the image, hoping to upgrade the conventional artificial retinas that only show black and white images to color images. For example, in U.S. Pat. No. 7,840,274 B2, the artificial retina comprises a color image receiver for receiving a color image and converting the color image into an electrical signal, and an image processing unit coupled to the color image receiver for processing the electrical signal. In the patent, a plurality of pixel electrodes are driven by data from the image processing unit to stimulate the optic nerve by time mode to produce a perception of color images. As far as we know, however, there is no published evidence that the time mode stimulation scheme as described in said patent works universally, reliably, or at all.

At present, a number of pixel units of the artificial retina continues to increase, which has been greatly advanced for artificial retinas having only a few tens of pixel units in the past. In contrast, related researches on artificial retinal systems that provide color visual perception are still at a very early stage, and even though many manufacturers and teams have proposed various artificial retinal systems that provide color visual perception, there is no corresponding product/system that has been manufactured, or it is not good enough to achieve color visual perception after practical operations. Obviously, there is still a lot of room for development in developing artificial retina systems providing color visual perception, depending on the continuous investment and improvement of relevant teams.

SUMMARY OF THE INVENTION

The present invention is an artificial retinal prosthesis to electrically stimulate a retina of an eye by a spatiotemporal electrical stimulation. The artificial retinal prosthesis comprises a plurality of pixel group units arranged in an array for inducing perception of different colors. Each of the pixel group units comprises a main pixel unit and at least one surrounding pixel unit adjacent to the main pixel unit, which are configured to receive an external visual image entering eyes of the user. The main pixel unit and the surrounding pixel unit respectively outputs an electrical stimulation waveform according to a first stimulation cycle and a second stimulation cycle respectively to retinal cells of the user for inducing a color perception. The first stimulation cycle of the main pixel unit has a first-half duration and a second-half duration after the first-half duration, the first-half duration of the first stimulation cycle has inactive period greater than 20% and less than 80% and the rest of the first stimulation cycle is active period, and the second-half duration of the first stimulation cycle is inactive period. The second stimulation cycle of the surrounding pixel unit has a first-half duration and a second-half duration after the first-half duration, the first-half duration of the second stimulation cycle is active period and the second-half duration of the second stimulation cycle is inactive period.

The system for artificial retinal prosthesis of the present invention causes the stimulation of the pixel electrodes and the spectrum of the external visual image entering the user's eyes to change synchronously along with different time sequences and different spatiotemporal distributions of each retinal cell, thereby stimulating the patient's retinal cells to provide the patient with a color image perception that assists the patient in truly obtaining RGB color vision. The spatiotemporal stimulation creates color perception in essential the same way as the so-called Fechner Color effect.

BRIEF DESCRIPTION OF THE DRAWINGS

FIG. 5 is a schematic view showing the states in which pixel electrodes are turned on and off according to embodiment 3 of the present invention;

FIG. 6 is a schematic view showing the states in which the pixel electrodes are turned on and off according to embodiment 4 of the present invention;

DETAILED DESCRIPTION OF THE PREFERRED EMBODIMENTS

Figure 1:
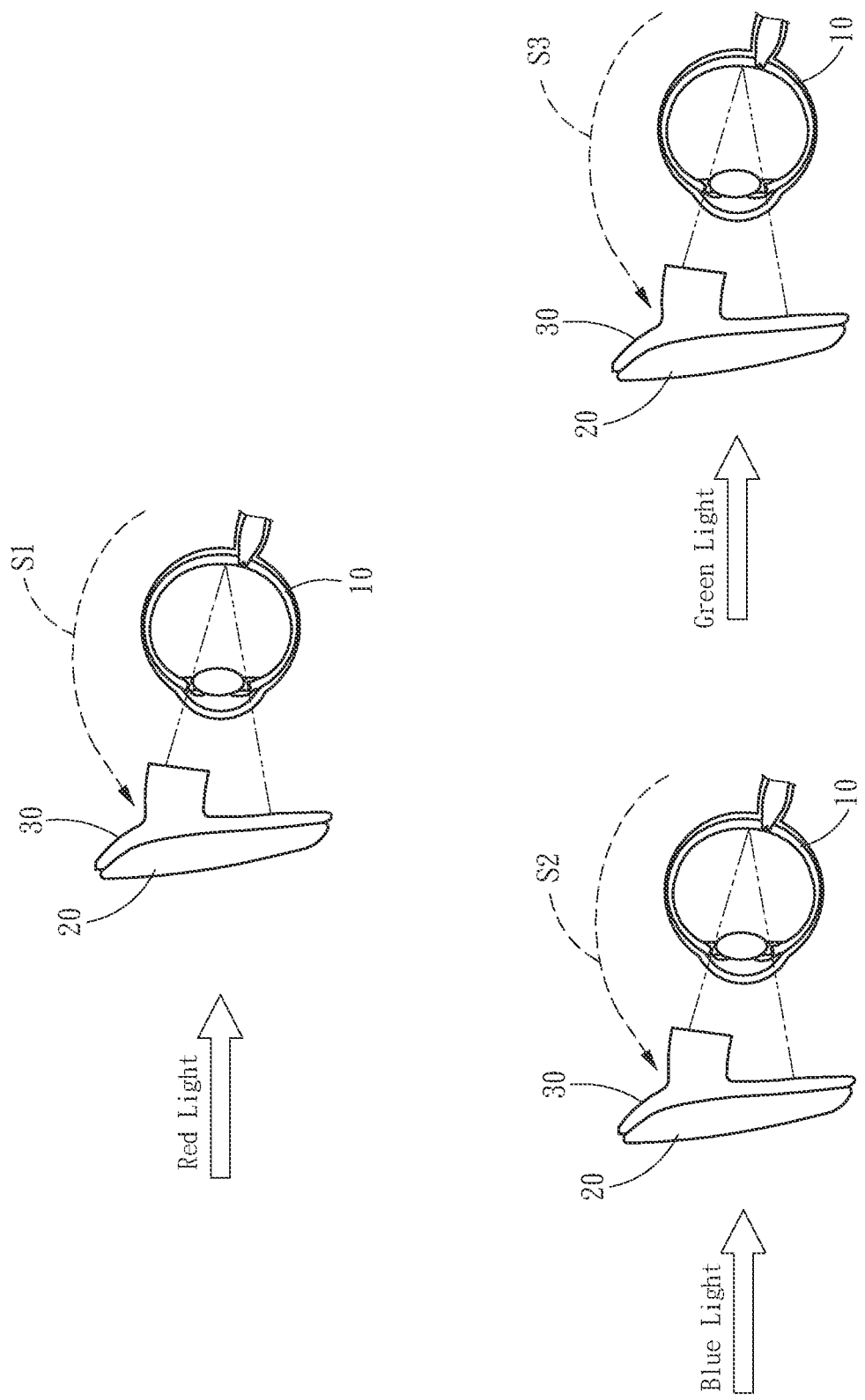
FIG. 1 is a schematic diagram of the operation of a system for artificial retinal prosthesis with color vision according to an embodiment of the present invention.

Referring to FIG. 1. A system for artificial retinal prosthesis with color vision in an embodiment of the present invention mainly comprises an artificial retinal prosthesis 10 and a color shutter 20, and the color shutter 20 is fitted on a goggle 30. In other embodiments, the color shutter 20 can also be fitted to a pair of glasses or other devices that can be worn by a user.

The artificial retinal prosthesis 10 can send a wireless signal to the goggle 30 to control the color shutter 20 of the goggle 30. For example, when the artificial retinal prosthesis 10 needs a red light stimulus, the artificial retinal prosthesis 10 sends a wireless signal S1 to the goggle 30 to activate a red color shutter in the color shutter 20, so that only red light can pass through the red color shutter of the goggle 30 to reach the artificial retinal prosthesis 10. If a blue light stimulus is required, the artificial retinal prosthesis 10 sends a wireless signal S2 to the goggle 30 to activate a blue color shutter in the color shutter 20, so that blue light can pass through the goggle 30 to reach the artificial retinal prosthesis 10. Likewise, when a green light stimulus is required, the artificial retinal prosthesis 10 sends a wireless signal S3 to the goggle 30 to activate a green color shutter, so that green light can pass through the goggle 30 to reach the artificial retinal prosthesis 10. Subsequently, after the artificial retinal prosthesis 10 receives a specific incident light such as red light, blue light, or green light through the color shutter 20, a pixel electrode array in the artificial retinal prosthesis 10 is electrically stimulated by a spatiotemporal electrical stimulation.

When the pixel electrodes in the artificial retinal prosthesis 10 are defined as Pxy according to the spatial positions, such as P11, P12, P13, P22, P23, the above-mentioned "spatiotemporal electrical stimulation" refers to different stimulations given to corresponding optic nerves by different Pxy at different times, for example, P11 and P12 stimulations are given at time point t1, but the remaining pixel electrodes are not.

The artificial retinal prosthesis 10 is disposed on the retina of the eye structure, and can be disposed on the sub-retina or the epi-retina as needed in actual use without particular limitation. This embodiment is disposed on the sub-retina. The artificial retinal prosthesis 10 comprises a plurality of pixel arrays and a processing module disposed correspondingly to the plurality of pixel arrays. Each of the plurality of pixel arrays comprises a substrate and a plurality of sub-pixels disposed on the substrate for receiving a color image. In this embodiment, the substrate can be a thin flexible silicon substrate that can be deformed and bent as desired, so that it can be bent as much as possible into a structure conforming to the shape of a human eye and disposed in the eye of a patient.

In actual manufacturing, for example, the substrate can be fabricated based on a manufacturing process using a Silicon On Insulator (SOI) chip, and formed by thinning the chip after a Metal-Oxide-semiconductor (MOS) fabrication. The processing module can include a correlated double sampling unit (CDS), an analog-to-digital converter (ADC), a digital core, and a digital-to-analog converter (DAC) to process a signal of the pixel array. However, the components included in the processing module are not limited to the above components, technicians of this field can add or delete based on actual needs and designs.

Each of the plurality of sub-pixels comprises at least one pixel electrode, a photodiode, and a circuit architecture electrically connected to the photodiode. After an incident light emit to the photodiode, the incident light is converted into an electric charge and a photovoltaic potential, and a light-induced electrical stimulation signal is generated according to an intensity ratio of the incident light. The light-induced electrical stimulation signal generates the spatiotemporal electrical stimulation to stimulate the patient's retinal cells, thereby producing a color image.

It should be additionally explained that, in another embodiment of the present invention, the color shutter 20 may not be assembled on the goggle 30, but can be integrated into a single structure with the artificial retinal prosthesis 10. That is, the color shutter 20 can be formed on the pixel array of the artificial retinal prosthesis 10 and can include a plurality of optical shutter units corresponding to different colors. For example, the color shutter 20 can include red shutters formed in a first row to a third row of the pixel array, green shutters formed in a fourth row to a sixth row, and blue shutters formed in a seventh row to a ninth row.

Figure 2:
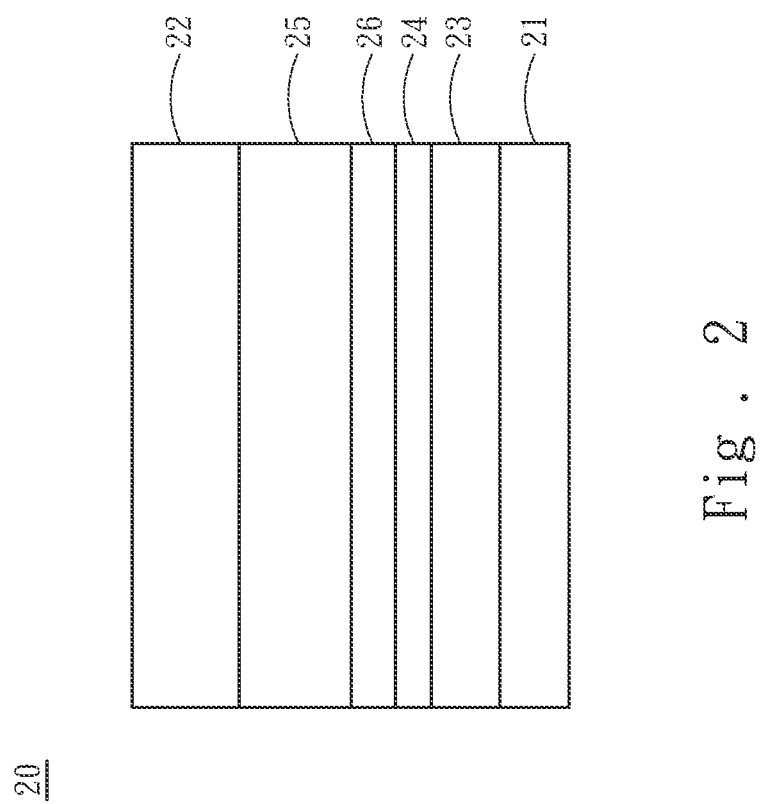
FIG. 2 is a color shutter structure according to an embodiment of the present invention.

For one of the examples of the color shutter 20, please refer to FIG. 2. The color shutter 20 can include a first substrate 21, a second substrate 22 disposed oppositely to the first substrate 21, an electrode 23 disposed between the first substrate 21 and the second substrate 22, a hydrophobic layer 24 disposed between the electrode 23 and the second substrate 22, a first fluid layer 25 disposed between the hydrophobic layer 24 and the second substrate 22, and a second fluid layer 26 disposed between the hydrophobic layer 24 and the first fluid layer 25, wherein the first fluid layer 25 and the second fluid layer 26 are immiscible with each other.

In this embodiment, the first substrate 21 and the second substrate 22 are transparent and can be formed with the same or different materials, such as glass, resin, polycarbonate (PC), and the like.

The first fluid layer 25 can be a conductive or polarized water or salt solution; and the second fluid layer 26 can be an oily medium, so that when the first fluid layer 25 and the second fluid layer 26 coexist between the second substrate 22 and the hydrophobic layer 24, a two-layer structure can be formed without being miscible. In this embodiment, the second fluid layer 26 can be a mixture of oils with different colors, such as can be selected from a green oil, a red oil, a blue oil, or any combinations of the above oils.

The hydrophobic layer 24 can be a functional layer with low surface energy and high stability, and specifically, can be made of a polymer or a silicon dioxide layer. For example, the polymer used for the hydrophobic layer 24 may be a fluoropolymer such as Cytop or amorphous Teflon, or a hydrocarbon polymer may also be used. If silicon dioxide is used, its surface needs to be treated hydrophobically.

The electrode 23 is disposed on the first substrate 21 to apply a voltage to the first fluid layer 25. The electrode 23 used in the present embodiment is preferably a transparent electrode made of any suitable conductive material such as indium tin oxide (ITO). The above is merely illustrative, and the present invention is not limited thereto, and the color shutter 20 may employ other devices such as a light filter.

In another embodiment of the present invention, the color shutter 20 can further include an optical sensor for sensing ambient light and/or a variable light filter for automatically controlling light passing through the color shutter 20 according to environmental conditions.

The principle used by the color shutter 20 is an electrowetting effect, that is, a wettability of the oily medium on the substrate is controlled by changing a voltage between the oily medium and the hydrophobic layer 24 (insulating layer). More specifically, the oily medium is deformed and displaced by changing a contact angle. The term "wetting" used above refers to the process of a fluid on a solid surface being replaced by another fluid. The fluid on the solid surface (i.e., the hydrophobic layer 24) can diffuse, at this time, the adhesion of the fluid on the solid surface is greater than the cohesion, referred to as "wetting." Conversely, when the fluid on the solid surface (i.e., the hydrophobic insulating layer) cannot diffuse, the contact surface has a tendency to shrink into a spherical shape, which is called "non-wetting", and "non-wetting" refers to the adhesion of the fluid on the solid surface being smaller than the cohesion.

Figure 3:
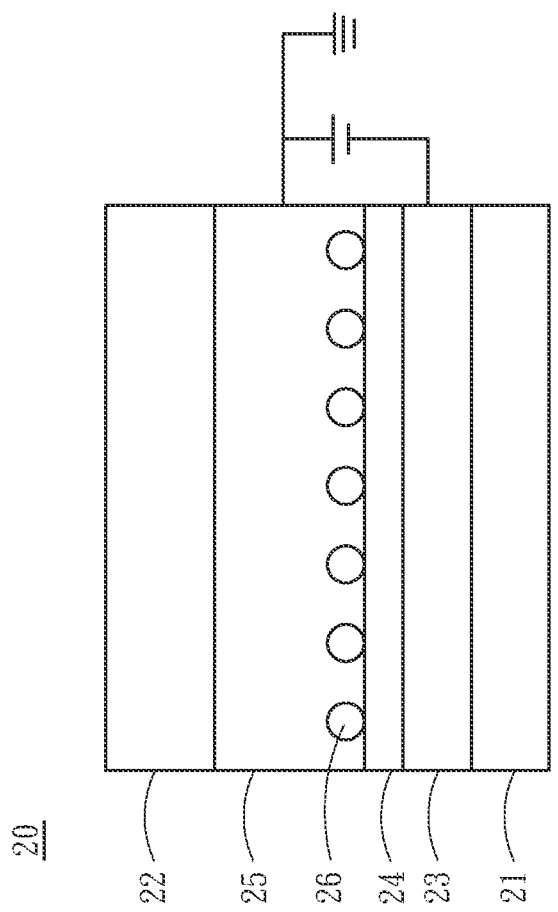
FIG. 3 is a schematic view showing an electric field applied to the color shutter structure of FIG. 2 of the present invention.

Returning to the present invention, the first fluid layer 25 and the second fluid layer 26 are immiscible with each other without applying an electric field to the fluids (closed state) to form a two-layer structure in which the first fluid layer 25 is diffused to form as a fluid layer adjacent to the second substrate 22; and the second fluid layer 26 also diffuses to form a fluid layer adjacent to the hydrophobic layer 24 and serves as color pixels. However, when an electric field is applied to the fluids (on state), the second fluid layer 26 is broken into small droplets to cause the color shutter 20 to exhibit a transparent color, as shown in FIG. 3.

Therefore, in order to obtain various display results, the second fluid layer 26 (i.e., the oily medium) can be designed to have a desired color, and a surface of the oily fluid can be controlled to change the pixels by controlling the voltage.

In the other embodiment, the anisotropic color pigment particles (say pigment needles) in fluid suspensions could be utilized in an alternative color shutter. Three shutters in tandem, with Yellow, Cyan, and Magenta color pigments, would be needed. Each color shutter would be turned on by applying sufficient large voltage across the fluid to align the particle with the field. Alternatively, another type of color shutter with electrophoretic cells in shutter mode could be used. This is somewhat harder to reach adequate speed, but can work with optimized cells.

When the system for artificial retinal prosthesis with color vision of this embodiment is in use, the color image is converted into the light-induced electrical stimulation signal by the photodiode of the sub-pixel, and the spatiotemporal electrical stimulation is generated to provide the patient with color perception. As a specific example, the spatiotemporal electrical stimulation of about 4 Hz to 8 Hz (preferably 7 Hz) can be divided into seven equally spaced phases within one cycle, producing color sensations of red (R), green (G) and blue (B).

Further explain how to provide the patient with color perception by the spatiotemporal electrical stimulation as below.

Embodiment 1

In this embodiment, the pixel electrodes in each of the pixel arrays are arranged in 1 column of 9 rows and classified into three groups corresponding to the specific color perceptions. A time series takes 7 equally spaced frames as a cycle, and the cycles per second (cps) can be between 7 and 8, so the frames per second (fps) are between 49 and 56, and the cycle between two of the frames is approximately 20 ms.

Please refer to Table 1, wherein "-" means the pixel electrode is turned off and "|" means the pixel electrode is turned on.

TABLE 1

|   | Frame | 1 | 2 | 3 | 4 | 5 | 6 | 7 |
|---|-------|---|---|---|---|---|---|---|
| R | Row 1 | — | — | — | \| | \| | \| | \| |
|   | Row 2 | — | — | — | — | — | \| | \| |
|   | Row 3 | — | — | — | \| | \| | \| | \| |
| G | Row 4 | — | — | — | \| | \| | \| | \| |
|   | Row 5 | — | — | — | — | \| | \| | — |
|   | Row 6 | — | — | — | \| | \| | \| | \| |
| B | Row 7 | — | — | — | \| | \| | \| | \| |
|   | Row 8 | — | — | — | \| | \| | — | — |
|   | Row 9 | — | — | — | \| | \| | \| | \| |

For the 3 rows of R/G/B strips, the span is 240 μm (30 m*8) strip width.

Row 1 to row 9 start rolling at the same time. It can be found from Table 1 that all the pixel electrodes are turned off in frame 1; the pixel electrodes of row 1, row 3 to row 9 are turned on while the other pixel electrodes are turned off in frame 5; while in frame 7, all the pixel electrodes are turned on except for the pixel electrodes of row 5 and row 8 being turned off. Based on the arrangement and operation of the pixel electrodes described above, the patient can perceive colors on the corresponding pixel electrodes, for example, in the cycles from frame 6 to frame 7, the patient can perceive red in the pixel electrodes of row 2.

Figure 4:
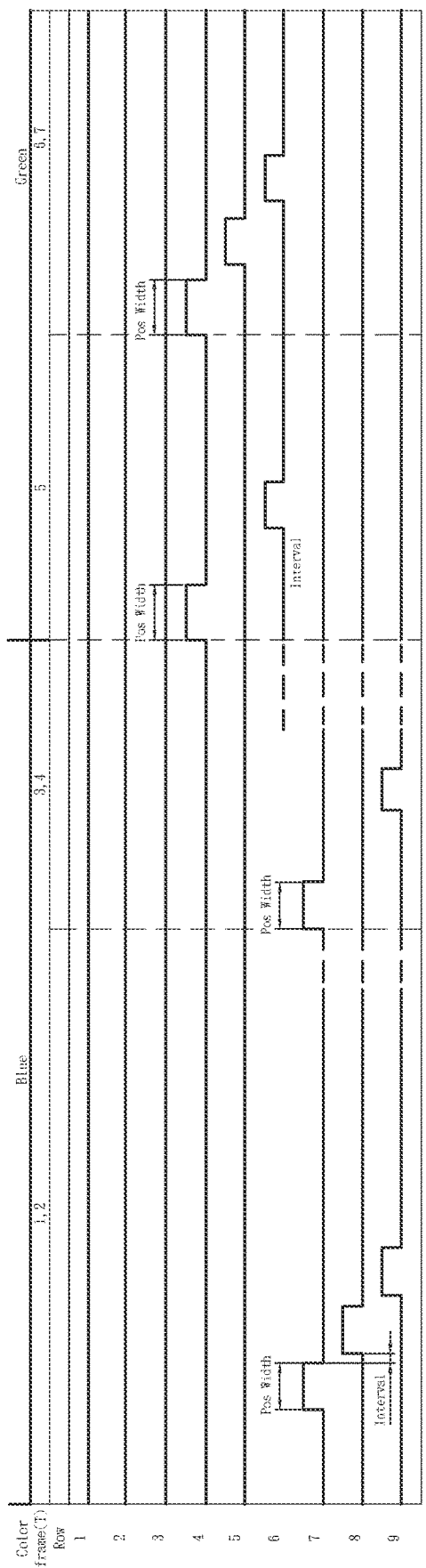
FIG. 4 is a schematic diagram of activation of row-to-row of the system for artificial retinal prosthesis with color vision according to an embodiment of the present invention.

If power attenuation problem is taken into consideration, in other embodiments, electrical stimulations of the above-mentioned "rows" are not simultaneously sent out in the same frame. If all the "rows" in the same frame are enabled at exactly the same time, the artificial retinal prosthesis 10 will consume a very large amount of power and cause a drop in power, even making the artificial retinal prosthesis 10 unable to function properly. In order to avoid the above problem, in the cycles of the same frame, when the state of the pixel electrodes is "|" representing being turned-on, they will be activated row-to-row. That is to say, electrical stimulations of the subsequent rows will slightly lag behind the previous pixel electrode; however, when the state of the pixel electrodes is "-" representing being turned-off, as in the first column to the third column (frame 1 to frame 3) of Table 1 above, the pixel electrodes in the columns cannot be activated and electrical stimulations are not sent out from the columns. Please refer to FIG. 4, where the horizontal axis (x-axis) is time and the vertical axis (y-axis) is electrical signal strength, that is, voltage. "Pulse width" in FIG. 4 refers to pulse duration, and "Interval" represents time delay. In Tables 1 and 2, the time for turning on each of the rows is simultaneous, but in reality, there may be a time difference between turning on each of the rows (such as the time delay of ns level), for example, after row 7 is turned on and off, then it is the turn for row 8 to be turned on and off.

Embodiment 2

Please refer to Table 2. In this embodiment, the pixel electrodes are arranged in 1 column of 6 rows, and the electrodes are classified into three groups with each of the groups respectively corresponding to a specific color. The setting of the time series in this embodiment is the same as that of Embodiment 1.

TABLE 2

|   | Frame | 1 | 2 | 3 | 4 | 5 | 6 | 7 |
|---|-------|---|---|---|---|---|---|---|
| R | Row 1 | — | — | — | — | — | \| | \| |
|   | Row 2 | — | — | — | \| | \| | \| | \| |

TABLE 2-continued

| | Frame | 1 | 2 | 3 | 4 | 5 | 6 | 7 |
|---|---|---|---|---|---|---|---|---|
| G | Row 3 | — | — | — | — | | | | | — |
| | Row 4 | — | — | — | | | | | | | | |
| B | Row 5 | — | — | — | | | | | | — | — |
| | Row 6 | — | — | — | | | | | | | | |

This embodiment is similar to that of Table 1, the pixel electrodes of row 1 to row 6 are all turned off in frame 1; the pixel electrodes of row 2 to row 6 are all turned on in frame 5, only the pixel electrodes of row 1 are turned off; while in frame 7, all the pixel electrodes are turned on except for the pixel electrodes of row 3 and row 5 being turned off.

Embodiment 3

Please refer to FIG. 5, wherein "D" represents a dummy electrode, "R" represents an electrode group that can perceive red correspondingly, "G" represents an electrode group that can perceive green correspondingly, and "B" represents an electrode group that can perceive blue correspondingly. In this embodiment, the pixel electrodes are arranged in 7 rows of 6 columns, and each of the R, G, B pixel electrodes is surrounded by 9 dummy electrodes.

If row 2 of column 3 is taken as an example, all the pixel electrodes are turned off in frame 1 to frame 4, and the surrounding dummy electrodes are also turned off; while the pixel electrodes are turned on in frame 5 to frame 6, so only green light can pass through the goggle 30 to reach the artificial retinal prosthesis 10, and at the same time, the surrounding dummy electrodes are also turned on. According to the operation of the pixel electrodes described above, the patient can have a green visual perception in the pixel electrodes of column 3 and row 2, and by the above arrangement of the dummy electrodes, a visual contrast can be generated between the pixel electrodes corresponding to the specific colors and the surrounding areas thereof, and the effect of enhancing the color perception of the patient is achieved.

Embodiment 4

Referring to FIG. 6, "D" represents a dummy electrode, "R" represents an electrode group that can perceive red correspondingly, "G" represents an electrode group that can perceive green correspondingly, and "B" represents an electrode group that can perceive blue correspondingly. In this embodiment, the pixel electrodes are arranged in 7 rows of 6 columns, and each of the R, G, B pixel electrodes is surrounded by 9 dummy electrodes.

The operation of this embodiment is basically the same as that of Embodiment 3. If row 4 of column 3 is taken as an example, all the pixel electrodes are turned off in frame 1 to frame 5, and the surrounding dummy electrodes are also turned off; while the pixel electrodes are turned on in frame 6 to frame 7, so only red light can pass through the goggle 30 to reach the artificial retinal prosthesis 10, and at the same time, the surrounding dummy electrodes are also turned on.

Embodiment 5

The electrodes of the present embodiment are arranged in 1 column of 132 rows, and are divided into four groups, which respectively are "D" representing a dummy electrode, "R" representing an electrode group that can perceive red correspondingly, "G" representing an electrode group that can perceive green correspondingly, and "B" representing an electrode group that can perceive blue correspondingly. Wherein, each of the R, G, and B pixel electrodes is surrounded by 2 dummy electrodes. A time series takes 12 frames as a cycle, the cycles per second (cps) are 6, so the frames per second (fps) are 72.

In Table 3, "-" means the pixel electrode is turned off and "|" means the pixel electrode is turned on. For example, if it is desired to enable a blue color shutter during frame 1 to frame 4 so that only blue light can pass through the goggle 30 and generate a specific electrical stimulus, in the cycles of frame 1, blue light is used to activate the pixel electrodes of row 7 to row 9, row 16 to row 18, row 25 to row 27, and row 34 to row 36. The operation of this embodiment is also substantially the same as or similar to that of the foregoing embodiment, and thus will not be described herein again.

TABLE 3

| | | Frame | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| | | Color shutter | | | | | | | | | | | |
| | | B color shutter | | | | G color shutter | | | | R color shutter | | | |
| D | Row 1 | — | — | — | — | — | — | — | — | | | | | | | | |
| R | Row 2 | — | — | — | — | — | — | — | — | | | | | | | | |
| D | Row 3 | — | — | — | — | — | — | — | — | | | | | | | | |
| D | Row 4 | — | — | — | — | | | | | | | | | — | — | — | — |
| G | Row 5 | — | — | — | — | | | | | | | | | — | — | — | — |
| D | Row 6 | — | — | — | — | | | | | | | | | — | — | — | — |
| D | Row 7 | | | | | | | | | — | — | — | — | — | — | — | — |
| B | Row 8 | | | | | | | | | — | — | — | — | — | — | — | — |
| D | Row 9 | | | | | | | | | — | — | — | — | — | — | — | — |
| D | Row 10 | — | — | — | — | — | — | — | — | | | | | | | | |
| R | Row 11 | — | — | — | — | — | — | — | — | | | | | | | | |
| D | Row 12 | — | — | — | — | — | — | — | — | | | | | | | | |
| D | Row 13 | — | — | — | — | | | | | | | | | — | — | — | — |
| G | Row 14 | — | — | — | — | | | | | | | | | — | — | — | — |
| D | Row 15 | — | — | — | — | | | | | | | | | — | — | — | — |
| D | Row 16 | | | | | | | | | — | — | — | — | — | — | — | — |
| B | Row 17 | | | | | | | | | — | — | — | — | — | — | — | — |
| D | Row 18 | | | | | | | | | — | — | — | — | — | — | — | — |
| D | Row 19 | — | — | — | — | — | — | — | — | | | | | | | | |
| R | Row 20 | — | — | — | — | — | — | — | — | | | | | | | | |
| D | Row 21 | — | — | — | — | — | — | — | — | | | | | | | | |
| D | Row 22 | — | — | — | — | | | | | | | | | — | — | — | — |
| G | Row 23 | — | — | — | — | | | | | | | | | — | — | — | — |
| D | Row 24 | — | — | — | — | | | | | | | | | — | — | — | — |
| D | Row 25 | | | | | | | | | — | — | — | — | — | — | — | — |
| B | Row 26 | | | | | | | | | — | — | — | — | — | — | — | — |
| D | Row 27 | | | | | | | | | — | — | — | — | — | — | — | — |
| D | Row 28 | — | — | — | — | — | — | — | — | | | | | | | | |
| R | Row 29 | — | — | — | — | — | — | — | — | | | | | | | | |
| D | Row 30 | — | — | — | — | — | — | — | — | | | | | | | | |
| D | Row 31 | — | — | — | — | | | | | | | | | — | — | — | — |
| G | Row 32 | — | — | — | — | | | | | | | | | — | — | — | — |
| D | Row 33 | — | — | — | — | | | | | | | | | — | — | — | — |
| D | Row 34 | | | | | | | | | — | — | — | — | — | — | — | — |
| B | Row 35 | | | | | | | | | — | — | — | — | — | — | — | — |
| D | Row 36 | | | | | | | | | — | — | — | — | — | — | — | — |
| D | Row 37 | — | — | — | — | — | — | — | — | | | | | | | | |
| R | Row 38 | — | — | — | — | — | — | — | — | | | | | | | | |
| D | Row 39 | — | — | — | — | — | — | — | — | | | | | | | | |
| D | Row 40 | — | — | — | — | | | | | | | | | — | — | — | — |
| G | Row 41 | — | — | — | — | | | | | | | | | — | — | — | — |
| D | Row 42 | — | — | — | — | | | | | | | | | — | — | — | — |
| D | Row 43 | | | | | | | | | — | — | — | — | — | — | — | — |
| B | Row 44 | | | | | | | | | — | — | — | — | — | — | — | — |
| D | Row 45 | | | | | | | | | — | — | — | — | — | — | — | — |
| D | Row 46 | — | — | — | — | — | — | — | — | | | | | | | | |
| R | Row 47 | — | — | — | — | — | — | — | — | | | | | | | | |
| D | Row 48 | — | — | — | — | — | — | — | — | | | | | | | | |
| D | Row 49 | — | — | — | — | | | | | | | | | — | — | — | — |
| G | Row 50 | — | — | — | — | | | | | | | | | — | — | — | — |
| D | Row 51 | — | — | — | — | | | | | | | | | — | — | — | — |
| D | Row 52 | | | | | | | | | — | — | — | — | — | — | — | — |

TABLE 3-continued

| | | Frame | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 |
| | | B color shutter | | | | G color shutter | | | | R color shutter | | | |
| B | Row 53 | | | | | — | — | — | — | — | — | — | — |
| D | Row 54 | | | | | — | — | — | — | — | — | — | — |
| D | Row 55 | — | — | — | — | — | — | — | — | | | | |
| R | Row 56 | — | — | — | — | — | — | — | — | — | — | | |
| D | Row 57 | — | — | — | — | — | — | — | — | | | | |
| D | Row 58 | — | — | — | — | | | | | — | — | — | — |
| G | Row 59 | — | — | — | — | | | — | — | — | — | — | — |
| D | Row 60 | — | — | — | — | | | | | — | — | — | — |
| D | Row 61 | | | | | — | — | — | — | — | — | — | — |
| D | Row 62 | — | — | — | — | | | | | — | — | — | — |
| B | Row 62 | | | — | — | — | — | — | — | — | — | — | — |
| D | Row 63 | | | | | — | — | — | — | — | — | — | — |
| D | Row 64 | — | — | — | — | — | — | — | — | | | | |
| R | Row 65 | — | — | — | — | — | — | — | — | — | — | | |
| D | Row 66 | — | — | — | — | — | — | — | — | | | | |
| D | Row 67 | — | — | — | — | | | | | — | — | — | — |
| G | Row 68 | — | — | — | — | | | — | — | — | — | — | — |
| D | Row 69 | — | — | — | — | | | | | — | — | — | — |
| D | Row 70 | | | | | — | — | — | — | — | — | — | — |
| B | Row 71 | | | — | — | — | — | — | — | — | — | — | — |
| D | Row 72 | | | | | — | — | — | — | — | — | — | — |
| D | Row 73 | — | — | — | — | — | — | — | — | | | | |
| R | Row 74 | — | — | — | — | — | — | — | — | — | — | | |
| D | Row 75 | — | — | — | — | — | — | — | — | | | | |
| D | Row 76 | — | — | — | — | | | | | — | — | — | — |
| G | Row 77 | — | — | — | — | | | — | — | — | — | — | — |
| D | Row 78 | — | — | — | — | | | | | — | — | — | — |
| D | Row 79 | | | | | — | — | — | — | — | — | — | — |
| B | Row 80 | | | — | — | — | — | — | — | — | — | — | — |
| D | Row 81 | | | | | — | — | — | — | — | — | — | — |
| D | Row 82 | — | — | — | — | — | — | — | — | | | | |
| R | Row 83 | — | — | — | — | — | — | — | — | — | — | | |
| D | Row 84 | — | — | — | — | — | — | — | — | | | | |
| D | Row 85 | — | — | — | — | | | | | — | — | — | — |
| G | Row 86 | — | — | — | — | | | — | — | — | — | — | — |
| D | Row 87 | — | — | — | — | | | | | — | — | — | — |
| D | Row 88 | | | | | — | — | — | — | — | — | — | — |
| B | Row 89 | | | — | — | — | — | — | — | — | — | — | — |
| D | Row 90 | | | | | — | — | — | — | — | — | — | — |
| D | Row 91 | — | — | — | — | — | — | — | — | | | | |
| R | Row 92 | — | — | — | — | — | — | — | — | — | — | | |
| D | Row 93 | — | — | — | — | — | — | — | — | | | | |
| D | Row 94 | — | — | — | — | | | | | — | — | — | — |
| G | Row 95 | — | — | — | — | | | — | — | — | — | — | — |
| D | Row 96 | — | — | — | — | | | | | — | — | — | — |
| D | Row 97 | | | | | — | — | — | — | — | — | — | — |
| B | Row 98 | | | — | — | — | — | — | — | — | — | — | — |
| D | Row 99 | | | | | — | — | — | — | — | — | — | — |
| D | Row 100 | — | — | — | — | — | — | — | — | | | | |
| R | Row 101 | — | — | — | — | — | — | — | — | — | — | | |
| D | Row 102 | — | — | — | — | — | — | — | — | | | | |
| D | Row 103 | — | — | — | — | | | | | — | — | — | — |
| G | Row 104 | — | — | — | — | | | — | — | — | — | — | — |
| D | Row 105 | — | — | — | — | | | | | — | — | — | — |
| D | Row 106 | | | | | — | — | — | — | — | — | — | — |
| B | Row 107 | | | — | — | — | — | — | — | — | — | — | — |
| D | Row 108 | | | | | — | — | — | — | — | — | — | — |
| D | Row 109 | — | — | — | — | — | — | — | — | | | | |
| R | Row 110 | — | — | — | — | — | — | — | — | — | — | | |
| D | Row 111 | — | — | — | — | — | — | — | — | | | | |
| D | Row 112 | — | — | — | — | | | | | — | — | — | — |
| G | Row 113 | — | — | — | — | | | — | — | — | — | — | — |
| D | Row 114 | — | — | — | — | | | | | — | — | — | — |
| D | Row 115 | | | | | — | — | — | — | — | — | — | — |
| B | Row 116 | | | — | — | — | — | — | — | — | — | — | — |
| D | Row 117 | | | | | — | — | — | — | — | — | — | — |
| D | Row 118 | — | — | — | — | — | — | — | — | | | | |
| R | Row 119 | — | — | — | — | — | — | — | — | — | — | | |
| D | Row 120 | — | — | — | — | — | — | — | — | | | | |
| D | Row 121 | — | — | — | — | | | | | — | — | — | — |
| G | Row 122 | — | — | — | — | | | — | — | — | — | — | — |
| D | Row 123 | — | — | — | — | | | | | — | — | — | — |
| D | Row 124 | | | | | — | — | — | — | — | — | — | — |
| B | Row 125 | | | — | — | — | — | — | — | — | — | — | — |
| D | Row 126 | | | | | — | — | — | — | — | — | — | — |
| D | Row 127 | — | — | — | — | — | — | — | — | | | | |
| R | Row 128 | — | — | — | — | — | — | — | — | — | — | | |
| D | Row 129 | — | — | — | — | — | — | — | — | | | | |
| D | Row 130 | — | — | — | — | | | | | — | — | — | — |
| G | Row 131 | — | — | — | — | | | — | — | — | — | — | — |
| D | Row 132 | — | — | — | — | | | | | — | — | — | — |

Figure 7:
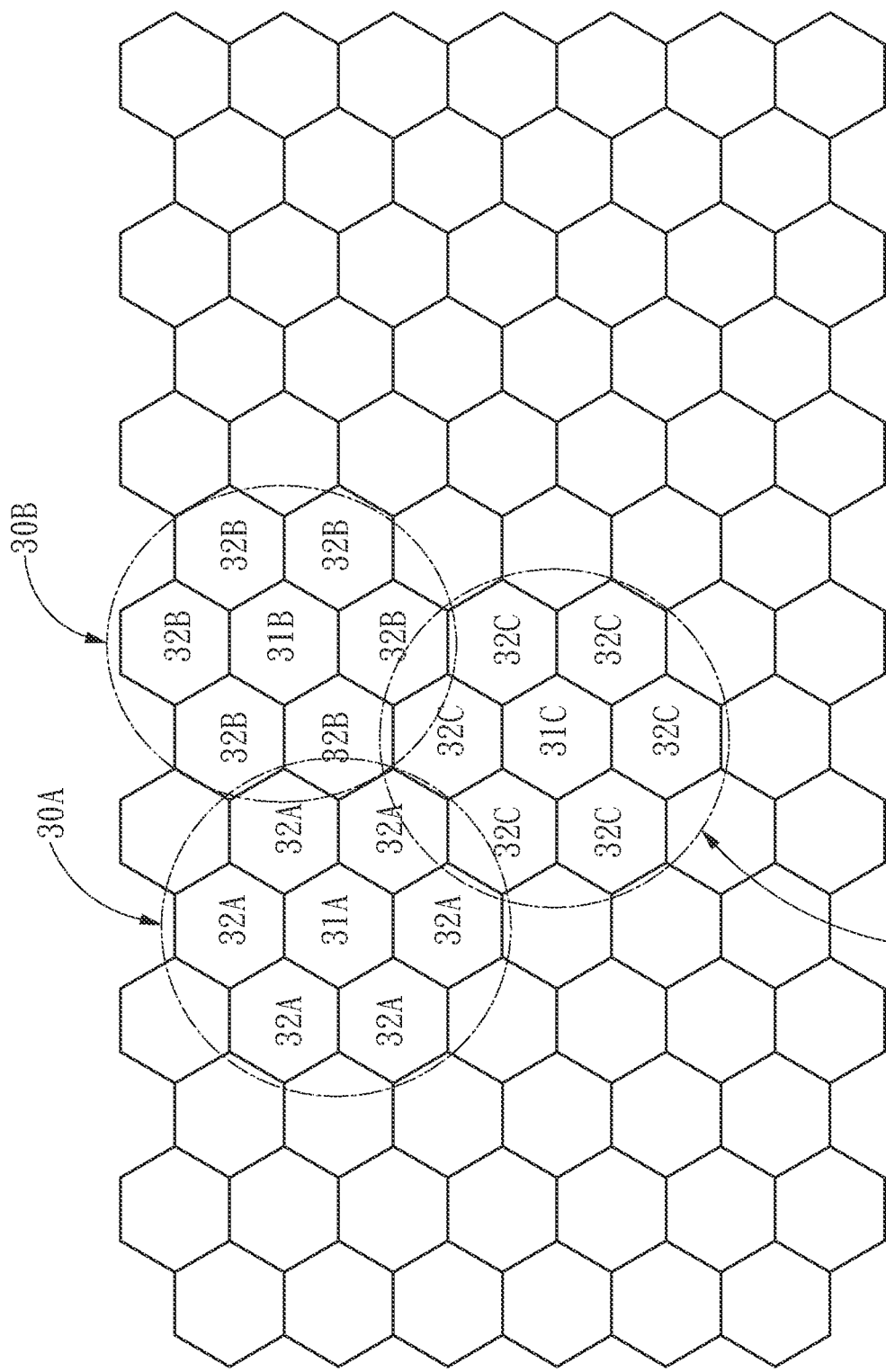
FIG. 7 illustrates an artificial retinal prosthesis according to an exemplary embodiment of the invention.

FIG. 7 illustrates an artificial retinal prosthesis according to an exemplary embodiment of the invention. The artificial retinal prosthesis is configured to electrically stimulate a retina of an eye by a spatiotemporal electrical stimulation. The details of the spatiotemporal electrical stimulation will be described below.

The artificial retinal prosthesis includes a plurality of pixel group units 30A, 30B, 30C arranged in an array. The pixel group units 30A, 30B, 30C are configured to receive an external visual image entering eyes of the user and for inducing perception of different colors.

The pixel group unit 30A comprises a main pixel unit 31A and at least one surrounding pixel unit 32A adjacent to the main pixel unit 30A. The pixel group unit 30B comprises a main pixel unit 31B and at least one surrounding pixel unit 32B adjacent to the main pixel unit 30B. The pixel group unit 30C comprises a main pixel unit 31C and at least one surrounding pixel unit 32C adjacent to the main pixel unit 30C. In this embodiment, the pixel unit is formed in a hexagonal shape. In other embodiments, the pixel unit may be formed in a substantially elongated, circular, elliptic, triangular, quadrangular, pentagonal, heptagonal or octagonal shape.

In this embodiment, the first closest pixel unit to the main pixel is defined as the surrounding pixel unit. In other embodiments, the Nth closest pixel unit (e.g., N=2, 3, 4, 5, 6 . . . ) to the main pixel may be defined as the surrounding pixel unit.

Figure 8:
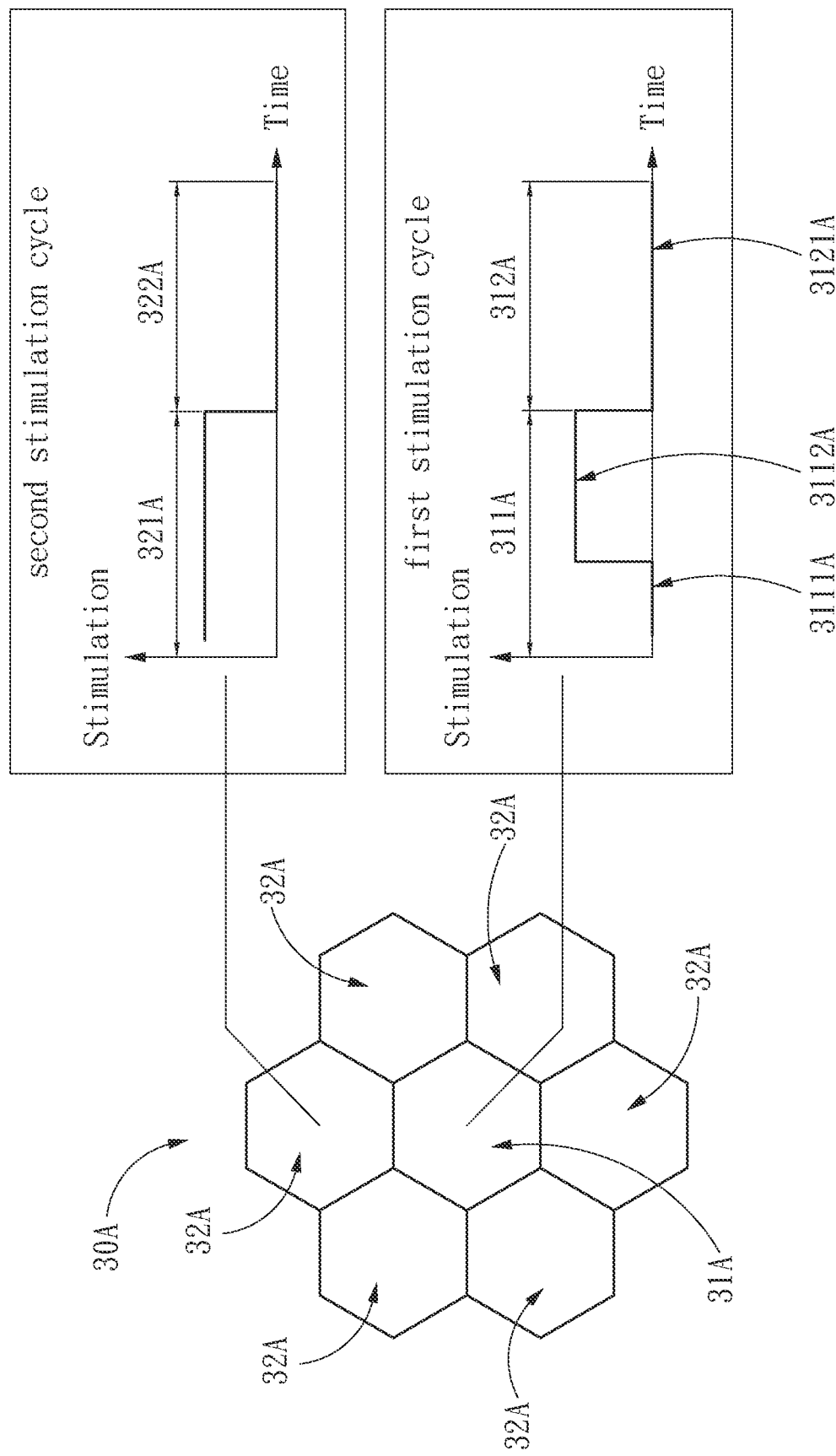
FIG. 8 illustrates a pixel group unit with stimulation cycle according to an exemplary embodiment of the invention.

FIG. 8 illustrates a pixel group unit with stimulation cycle according to an exemplary embodiment of the invention. Taking the pixel group unit 30A as the example. The main pixel unit 31A and the surrounding pixel units 32A at different locations respectively output an electrical stimulation waveform according to different stimulation cycles to create a color perception.

The main pixel unit 31A and the surrounding pixel units 32A output a first stimulation cycle and a second stimulation cycle respectively to retinal cells of the user. The first stimulation cycle of the main pixel unit 31A has a first-half duration 311A and a second-half duration 312A after the first-half duration 311A. The second stimulation cycle of the surrounding pixel unit 32A has a first-half duration 321A and a second-half duration 322A after the first-half duration 321A.

The first-half duration 311A of the first stimulation cycle has an inactive period 3111A greater than 20% and less than 80% of the first-half duration 311A and the rest of the first-half duration 311A is an active period 3112A, and the second-half duration 312A of the first stimulation cycle is an inactive period 3121A.

The second stimulation cycle of each of the surrounding pixel units 32A also has a first-half duration 321A and a second-half duration 322A after the first-half duration 321A, all the first-half duration 321A of the second stimulation cycle is active period and all the second-half duration 322A of the second stimulation cycle is inactive period.

In the above-mentioned, the active period refers to a period that electrode of the pixel unit outputs a stimulation to the retinal cells of the user and the inactive period refers to a period that electrode of the pixel unit does not output a stimulation to the retinal cells of the user.

In the present invention, each of the pixel group units is configured to produce a specific color of vision perception. The specific color may be red, blue or green. The color of vision perception produced by the pixel group unit depends on a sequence and a length of active period and inactive period in the first-half duration of the first stimulation cycle of the main pixel unit.

Figure 9:
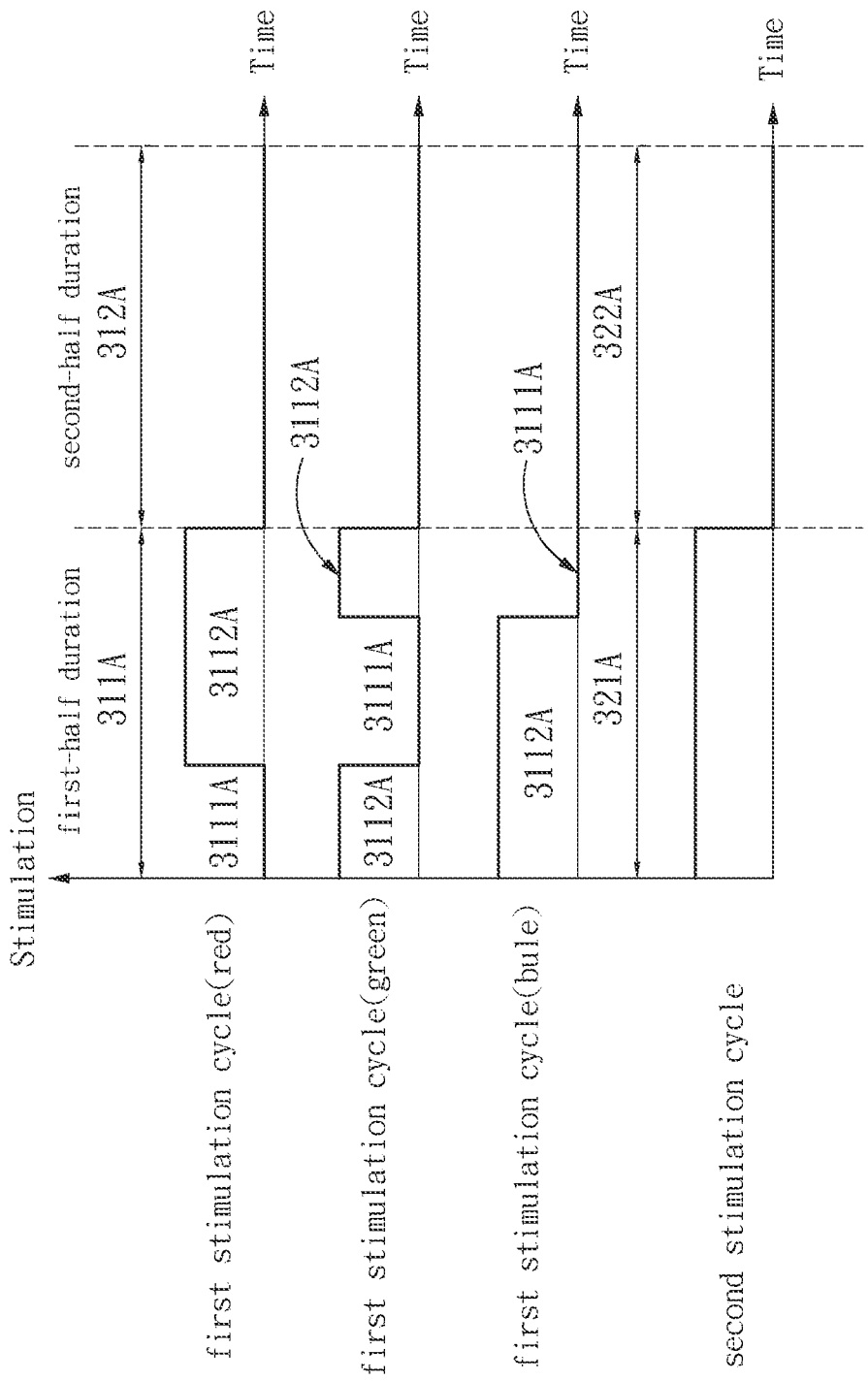
FIG. 9 illustrates various stimulation cycle for the main pixel unit and the surrounding pixel unit according to an exemplary embodiment of the invention.

FIG. 9 illustrates various stimulation cycle for the main pixel unit and the surrounding pixel unit according to an exemplary embodiment of the invention. In an embodiment of the invention, a red color perception can be produced when the first-half duration 311A of the main pixel unit 31A is consisted of the inactive period 3111A of approximately between 25% and 50% of the first-half duration 311A, followed by the active period 3112A. In an embodiment of the invention, a green color perception is produced when the first stimulation cycle 311A of the main pixel unit 31A is consisted of the active period 3112A greater than 25% of the first-half duration 311A, followed by the inactive period 3111A of approximately between 30% and 80% of the first-half duration 311A, followed by the active period 3112A. In an embodiment of the invention, a blue color perception is produced when the first-half duration 311A of the main pixel unit 31A is consisted of the active period 3112A of approximately between 20% and 80% of the first-half duration 311A, followed by the inactive period 3111A.

What is claimed is:

1. An artificial retinal prosthesis to electrically stimulate a retina of an eye by a spatiotemporal electrical stimulation, comprising:
    a plurality of pixel group units arranged in an array for inducing perception of different colors, each of the pixel group units comprising a main pixel unit and at least one surrounding pixel unit adjacent to the main pixel unit, which are configured to receive an external visual image entering eyes of the user;

wherein the main pixel unit and the surrounding pixel unit respectively output an electrical stimulation waveform according to a first stimulation cycle and a second stimulation cycle respectively to retinal cells of the user for inducing a color perception;

wherein the first stimulation cycle for the main pixel unit has a first-half duration and a second-half duration after the first-half duration, the first-half duration of the first stimulation cycle has an inactive period which is greater than 20% and less than 80% of the first-half duration, and the rest of the first-half duration is an active period, and the second-half duration of the first stimulation cycle is an inactive period; and wherein the second stimulation cycle for the surrounding pixel unit has a first-half duration and a second-half duration after the first-half duration, the first-half duration of the second stimulation cycle is an active period and the second-half duration of the second stimulation cycle is an inactive period.

2. The artificial retinal prosthesis as claimed in claim 1, wherein a red color perception is produced when the first-half duration of the main pixel unit consisted of the inactive period which is approximately between 25% and 50% of the first-half duration, followed by the active period.

3. The artificial retinal prosthesis as claimed in claim 1, wherein a green color perception is produced when the first-half duration of the main pixel unit consisted of the active period which is greater than 25% of the first-half duration, followed by the inactive period which is approximately between 30% and 50% of the first-half duration, followed by the active period.

4. The artificial retinal prosthesis as claimed in claim 1, wherein a blue color perception is produced when the first-half duration of the main pixel unit consisted of the active period which is approximately between 20% and 80% of the first-half duration, followed by the inactive period.

* * * * *